US00PP28721P3

(12) United States Plant Patent
Callahan

(10) Patent No.: US PP28,721 P3
(45) Date of Patent: Dec. 5, 2017

(54) APPLE TREE NAMED 'RKD'

(50) Latin Name: ***Malus domestica* Borkh**
Varietal Denomination: RKD

(71) Applicant: Callahan Orchards LLC, Royal City, WA (US)

(72) Inventor: Richard Callahan, Royal City, WA (US)

(73) Assignee: Callahan Orchards LLC

( * ) Notice: Subject to any disclaimer, the term of this patent is extended or adjusted under 35 U.S.C. 154(b) by 0 days.

(21) Appl. No.: 14/756,078

(22) Filed: Jul. 28, 2015

(65) Prior Publication Data

US 2017/0034974 P1 Feb. 2, 2017

(51) Int. Cl.
*A01H 5/08* (2006.01)

(52) U.S. Cl.
USPC ..... Plt./162

(58) Field of Classification Search
USPC ..... Plt./162
See application file for complete search history.

*Primary Examiner* — Keith Robinson
(74) *Attorney, Agent, or Firm* — Michelle Bos Legal LLC

(57) ABSTRACT

'RKD' is a Gala-type apple tree distinguished by its early maturing and early full-coloring fruit.

5 Drawing Sheets

Latin name: *Malus domestica* Borkh.
Variety denomination: 'RKD'.

BACKGROUND OF THE VARIETY:

'RKD' is a new and distinct variety of apple tree *Malus domestica* Borkh that originated as a spontaneous two-limb mutation of 'Tenroy' gala (U.S. Plant Pat. No. 4,121). 'RKD' was discovered by the inventor in a commercial apple orchard in Royal City, Wash. in 2006, and was selected for further observation because of its distinctive early maturing and early full-coloring fruit. Buds were taken from the distinctive limbs in 2007 and budded onto rootstock for further observation and evaluation. The variety has since been reproduced by budding at Royal City, Wash., and has been observed to remain true to type through successive asexually propagated generations.

BRIEF DESCRIPTION OF THE VARIETY

'RKD' is a Gala-type apple tree distinguished by its early maturing and early full-coloring fruit. A comparison of 'RKD' to 'Tenroy' and other Gala-type varieties 'Simmons Gala' (U.S. Plant Pat. No. 10,840), 'Banning Gala' (U.S. Plant Pat. No. 13,753) and 'Waliser Gala' (U.S. Plant Pat. No. 8,673) is shown in Table 1.

TABLE 1

Comparison of 'RKD' to Gala-type Varieties

| | 'Tenroy' | 'Simmons Gala' | 'Banning Gala' | 'Waliser Gala' | 'RKD' |
|---|---|---|---|---|---|
| Harvest timing | 0 | −3 days | −1 day | −3 days | −21 days |
| % Color Stripe/ Blush | 60% Orange/red stripe | 80% Dark red blush | 70% Dark red stripe/blush | 70% Narrow stripe over light red blush | 80% Red stripe over blush |

TABLE 1-continued

Comparison of 'RKD' to Gala-type Varieties

| | 'Tenroy' | 'Simmons Gala' | 'Banning Gala' | 'Waliser Gala' | 'RKD' |
|---|---|---|---|---|---|
| Bloom Time | 0 | 1-2 days after 'Tenroy' | 0 | 2 days after 'Tenroy' | 4-5 days after 'Tenroy' |
| # of Picks | 3 | 1 to 2 | 2 | 2 | 1 to 2 |
| Fruit Shape | Conical | Conical | Conical | Conical | Globose conical |
| Branching Habit | Good branching | Good branching | Good branching | Good branching | Reduced branching |
| Overall Tree Vigor | 100% | 95% | 100% | 95% | 90% |

BRIEF DESCRIPTION OF THE PHOTOGRAPHS

The photographs show two- and three-year-old trees, and were taken during the 2013 and 2014 growing seasons at Royal City, Wash.

DETAILED BOTANICAL DESCRIPTION OF THE VARIETY

Figure 1:
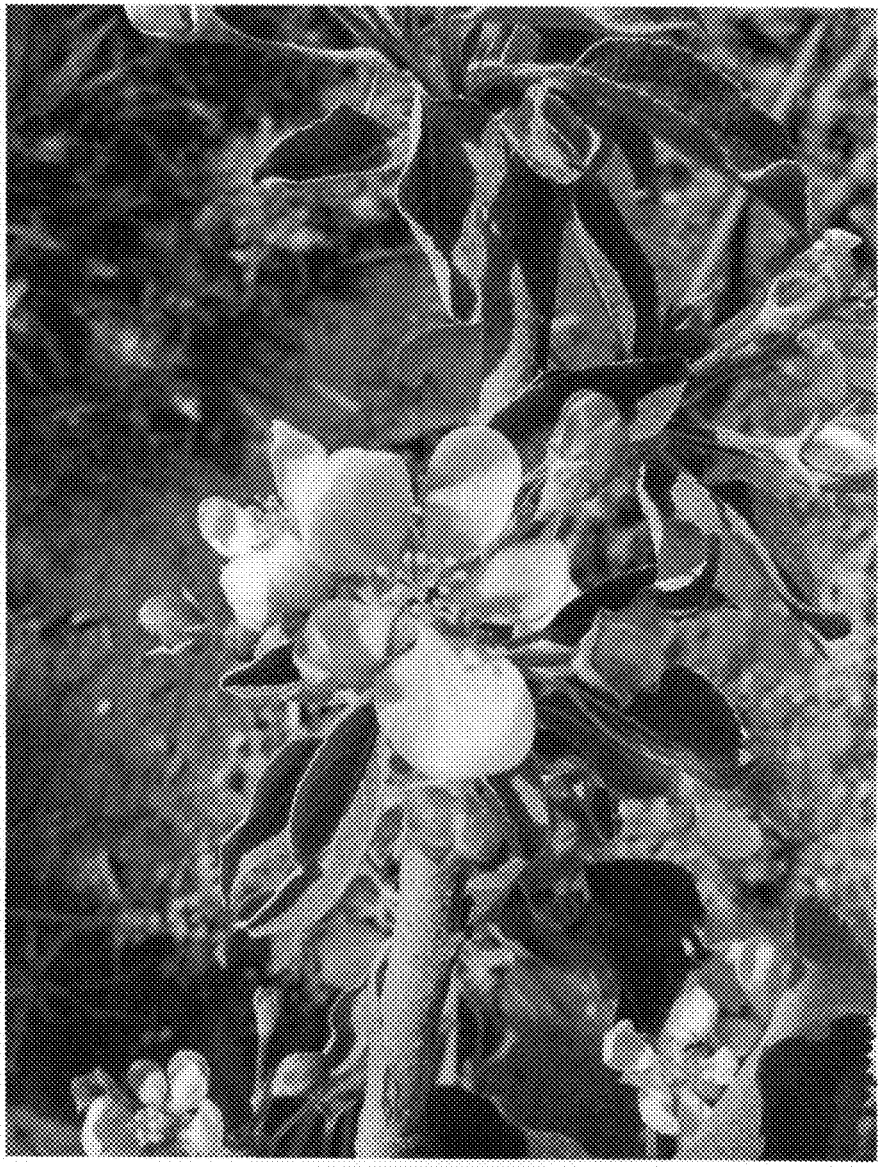
FIG. 1 shows a blossom, buds and young leaves on an 'RKD' apple tree.
Figure 2:
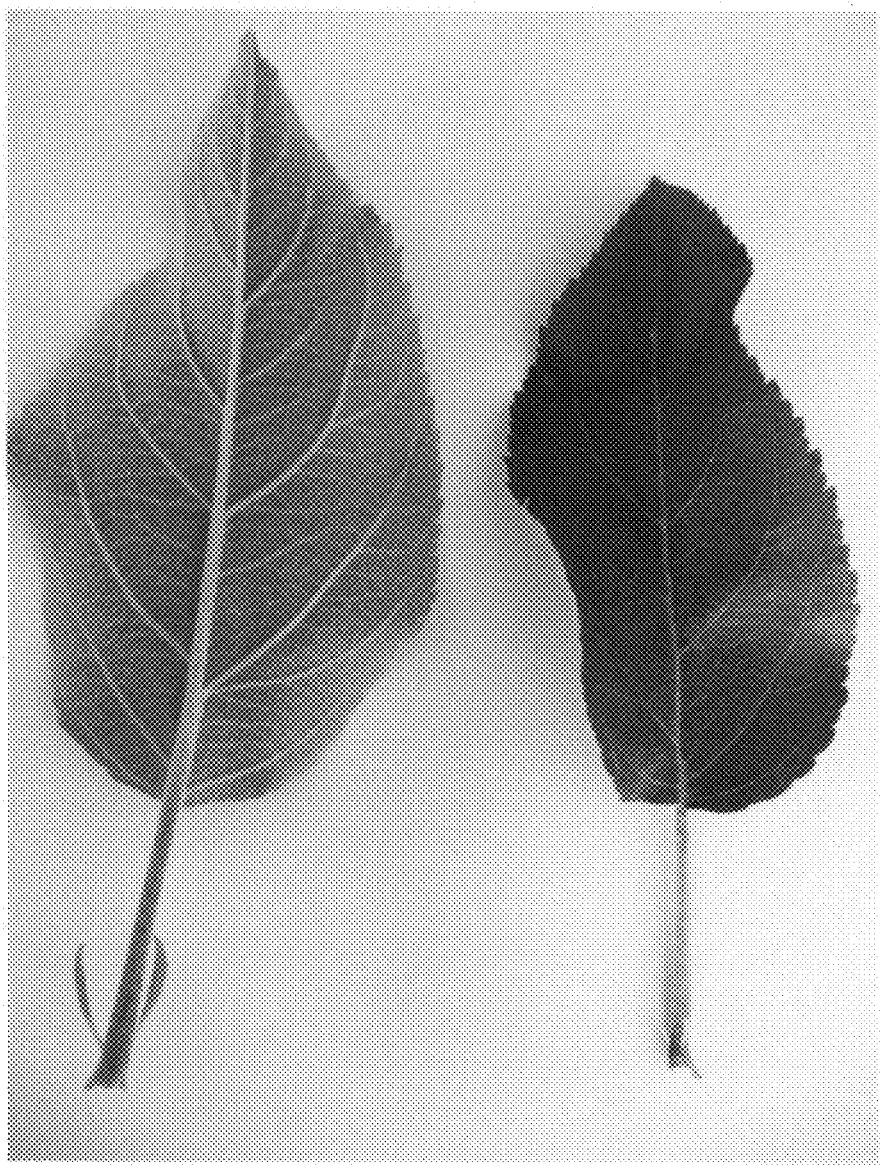
FIG. 2 shows the upper and lower surfaces of a leaf from an 'RKD' apple tree.
Figure 3:
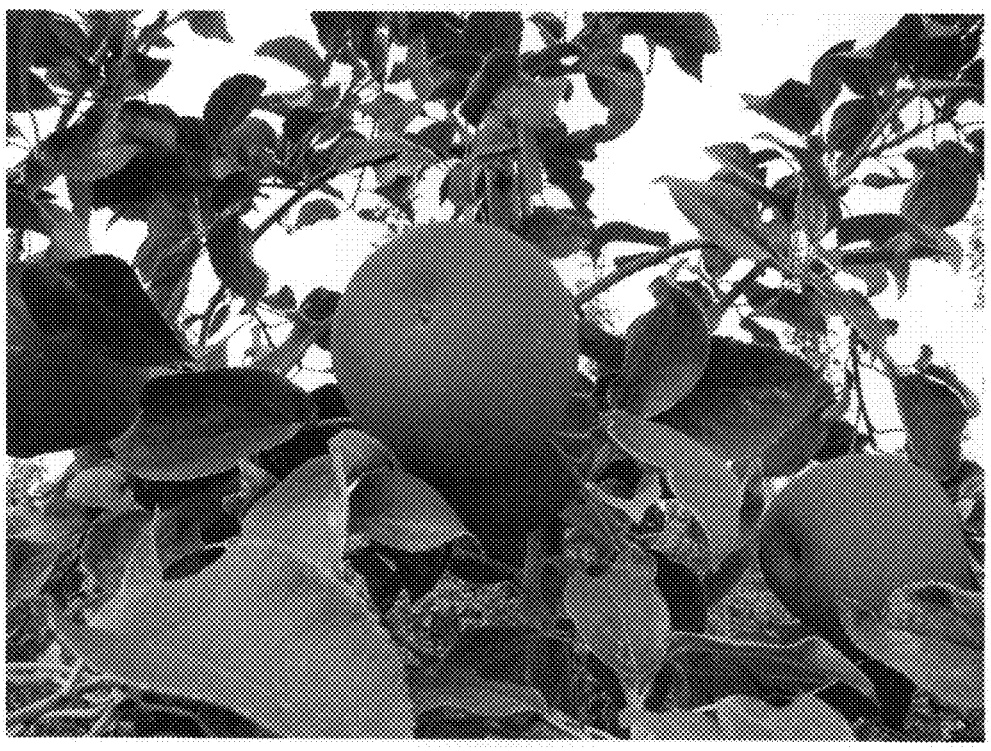
FIG. 3 shows fruit and leaves on an 'RKD' apple tree.
Figure 4:
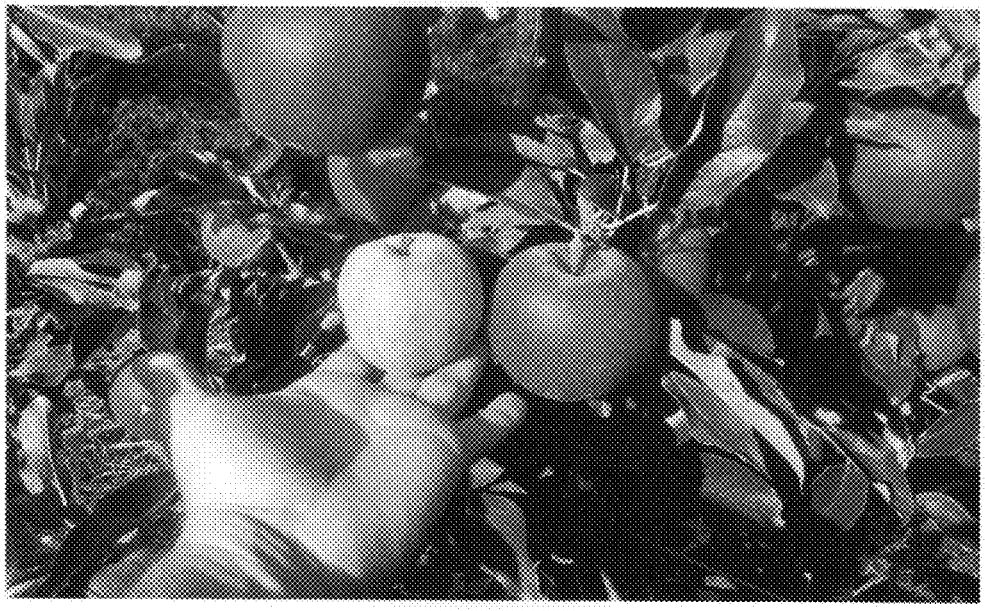
FIG. 4 shows a single 'Simmons Gala' apple next to 'RKD' apples on the tree.
Figure 5:
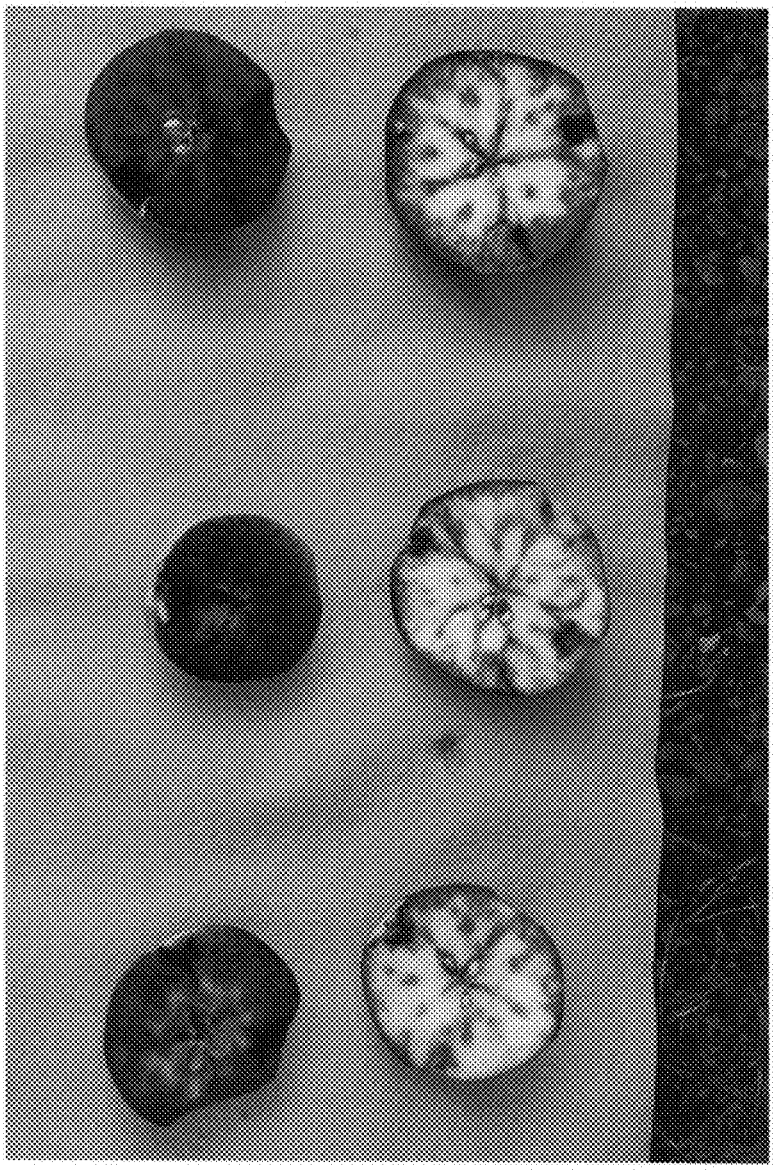
FIG. 5 shows a starch (maturity) test comparison of 'RKD' apples (left) and 'Simmons Gala' apples (right).

The following detailed botanical description is based on observations made during the 2013 and 2014 growing seasons at Royal City, Wash. of trees growing on 'Cepiland' rootstock (U.S. Plant Pat. No. 7,715), planted in 2011. All colors are described according to The Royal Horticultural Society Colour Chart (Fifth edition, 2007). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor*.—Moderate.
- *Type*.—Non-spur.
- *Habit*.—Moderate spreading.
- *Height*.—2.4 m.
- *Trunk diameter* (*at* 30 *cm above the graft*).—3.3 cm.
- *Bark texture*.—Smooth.
- *Bark color*.—Brown 200C.

Branch (fruiting branches located at around 1 m above the graft union):
- *Length*.—73 cm.
- *Diameter*.—16 mm.
- *Crotch angle*.—60 degrees from vertical.
- *Bark color*.—Brown 200C.
- *Lenticel length*.—1 mm.
- *Number of lenticels per* $cm^2$.—5.

One year old shoot:
- *Color*.—Brown 200D.
- *Pubescence*.—Moderate.
- *Thickness*.—9 mm to 11 mm.
- *Internode length*.—30 mm.
- *Pubescence*.—Slight.
- *Number of lenticels per* $cm^2$.—4.

Flower buds:
- *Quantity per spur*.—5.
- *Shape*.—Oblong, rounded.
- *Length*.—7 mm.
- *Diameter*.—5 mm.
- *Color*.—Red-purple N57B.
- *Color at balloon stage*.—Red-purple N57C.

Flowers:
- *Diameter of fully open flower*.—Medium (king bloom), avg. 45.1 mm.
- *Relative position of petal margin*.—Touching to overlapping.
- *Number per cluster*.—5 to 6.
- *Date of first bloom*.—Midseason, 3 days after 'Simmons Gala' (U.S. Plant Pat. No. 10,840).
- *Date of full bloom*.—4 days after 'Simmons Gala'.
- *Pollination requirement*.—Pollinator required.

Petals:
- *Number per flower*.—5.
- *Shape*.—Orbicular.
- *Length*.—2.2 to 3.0 cm.
- *Width*.—1.7 cm.
- *Apex*.—Obtuse.
- *Base*.—Pointed.
- *Margin*.—Smooth.
- *Coloration of upper surface*.—White N155D.
- *Coloration of lower surface*.—White N155C.

Pistils:
- *Size*.—Medium, length 16 mm.
- *Color*.—Yellowish green 145C.

Stigma:
- *Size*.—Small, diameter 0.3 mm.
- *Color*.—Yellow-green 150B.

Style:
- *Size*.—Medium, length 13.7 mm.
- *Color*.—Yellow-green 145C.

Ovary:
- *Size*.—Small, length 2.2 mm, diameter 2.2.
- *Color*.—Yellow-green 145B.

Anthers:
- *Quantity*.—15 to 17.
- *Size*.—Medium, length 2 mm.
- *Pollen*.—Present, moderately abundant (similar to other Gala-type varieties).
- *Color of pollen*.—Yellow 3B.

Pedicel:
- *Length*.—27 mm.
- *Diameter*.—1.8 to 2.4 mm.
- *Color*.—Yellow-green 145B.

Sepals:
- *Quantity*.—5.
- *Coloration*.—Yellow-green 144C.
- *Shape*.—Pointed.
- *Margin*.—Smooth.

Leaves:
- *Shape*.—Ovate.
- *Length*.—101 mm.
- *Width*.—60 mm.
- *Blade margin*.—Serrate.
- *Apex*.—Acuminate.
- *Base shape*.—Oblique.
- *Color of upper surface*.—Green 143 B.
- *Color of lower surface*.—Green 141A.
- *Attitude in relation to shoot*.—Outward to upward.

Petiole:
- *Length*.—3.1 cm.
- *Diameter*.—2 mm.
- *Coloration*.—Green 141C.

Fruit:
- *Quantity per cluster*.—1 to 2.
- *Height*.—75 mm to 80 mm.
- *Diameter*.—75 mm.
- *Weight*.—203 g.
- *Ratio of height to width*.—Nearly equal.
- *General shape in profile*.—Round to oblate.
- *Position of maximum diameter*.—Middle.
- *Ribbing*.—Slight.
- *Crowning at calyx end*.—Moderate.
- *Size of eye*.—1.1 cm.
- *Aperture of eye*.—Closed to partially open.
- *Length of sepal*.—5 mm.
- *Bloom of skin*.—Very slight.
- *Greasiness of skin*.—Very weak.
- *Background color of skin*.—Yellow 4B.
- *Amount of over color*.—90% or more.
- *Over color of skin*.—Red 46C.
- *Intensity of over color*.—Strong.
- *Pattern of over color*.—Blush over light striping.
- *Amount of russet around stalk cavity*.—Minimal.
- *Amount of russet on cheeks*.—None.
- *Area of russet around eye basin*.—None.
- *Length of stalk*.—1.8 mm to 3.0 cm.
- *Thickness of stalk*.—2.8 mm.
- *Depth of stalk cavity*.—17 mm.
- *Width of stalk cavity*.—Narrow, 10 mm.
- *Depth of eye basin*.—7.5 mm.
- *Width of eye basin*.—2.0 mm to 2.2 mm.
- *Firmness of flesh*.—Firm, 18+ lbs. at harvest.

*Flesh texture*.—Fine, crisp.
*Aperture of locules*.—Fully open.
*Aroma*.—Somewhat aromatic.
*Juiciness*.—High.
*Flesh coloration*.—Yellow 11D.
*Stem coloration*.—Red 53C.

Seeds:

*Quantity per fruit*.—1 to 2 per cell, 5 to 8 total.
*Size*.—Length 9 mm, width 0.5 mm.
*Texture*.—Firm, smooth.
*Shape*.—Tear drop.
*Coloration*.—Greyed-orange 164A.

Harvest:

*Time for harvest*.—August 3; 21+ days before 'Tenroy Gala'.
*Number of picks*.—1.
*Amount of fruit produced per tree per harvest*.—36 lbs. per tree (1500 trees/acre).
*Disease and pest resistance/susceptibility*.—No known resistance to disease or pest. Appears to be equal to its 'Tenroy Gala' in susceptibility to fireblight (*Erwinia amylovora*), powdery mildew (*Podosphaera leucotricha*), bitter pit (calcium disorders). Susceptibility to apple scab (*Venturia inaequalis*) is unknown as the disease is not prevalent in the area tested.

Market use: Fresh market.

I claim:

1. A new and distinct apple tree substantially as described and illustrated herein.

* * * * *